United States Patent
Schroeder et al.

(10) Patent No.: US 9,867,788 B2
(45) Date of Patent: Jan. 16, 2018

(54) MULTI-CHAMBER CELLULAR MIXING AND DELIVERY SYSTEM AND METHOD

(75) Inventors: Tania M. Schroeder, Hastings, MN (US); Natalie Ann Sautner, Lino Lakes, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1119 days.

(21) Appl. No.: 13/382,703

(22) PCT Filed: Jul. 9, 2010

(86) PCT No.: PCT/US2010/041508
§ 371 (c)(1),
(2), (4) Date: Jan. 6, 2012

(87) PCT Pub. No.: WO2011/006056
PCT Pub. Date: Jan. 13, 2011

(65) Prior Publication Data
US 2012/0101472 A1    Apr. 26, 2012

Related U.S. Application Data

(60) Provisional application No. 61/224,363, filed on Jul. 9, 2009.

(51) Int. Cl.
*A61M 5/19* (2006.01)
*A61K 31/00* (2006.01)

(52) U.S. Cl.
CPC ............... *A61K 31/00* (2013.01); *A61M 5/19* (2013.01); *A61M 2210/167* (2013.01)

(58) Field of Classification Search
CPC .. A61M 5/165; A61M 5/2066; A61M 5/2448; A61M 5/284; A61M 5/31596; A61M 5/3294; A61M 5/46; A61M 2005/1652; A61M 2005/1655; A61M 2005/1657
USPC ......... 604/82, 83, 84, 85, 89, 187, 190, 191, 604/500, 506, 518, 519, 522; 606/79, 606/184, 186
See application file for complete search history.

(56) References Cited

U.S. PATENT DOCUMENTS 3,767,085 A * 10/1973 Cannon et al. ................. 222/82
3,859,999 A *  1/1975 Ishikawa ....................... 604/190
4,260,007 A     4/1981 Wellslager et al.
(Continued)

OTHER PUBLICATIONS

Engelholm et al. "Disaggregation of human solid tumours by combined mechanical and enzymatic methods." Br. Cancer (1985), 51, 93-98.*

(Continued)

*Primary Examiner* — Gerald Landry, II
(74) *Attorney, Agent, or Firm* — Bookoff McAndrews, PLLC

(57) ABSTRACT

A multi-chamber injection and treatment system includes a first chamber, a second chamber, a mixing element, and a needle portion. The first chamber is generally adapted to receive and advance various cells, while the second chamber is adapted to receive and advance adipose tissue, and can blend or reduce the size of the adipose tissue. The mixing element combines the constituents of the chambers and is in communication with the needle portion for driving the cellular mixture into a target tissue site, such as the mid-corpora of the male penis.

21 Claims, 10 Drawing Sheets

(56) References Cited

U.S. PATENT DOCUMENTS

| | | | | |
|---|---|---|---|---|
| 4,753,536 | A * | 6/1988 | Spehar | A61C 5/062 222/137 |
| 5,472,421 | A * | 12/1995 | Klearman et al. | 604/82 |
| 5,752,933 | A * | 5/1998 | Morrison | 604/116 |
| 6,020,196 | A * | 2/2000 | Hu et al. | 435/366 |
| 6,071,272 | A | 6/2000 | Hoffman et al. | |
| 6,080,173 | A * | 6/2000 | Williamson, IV | A61B 17/32053 600/567 |
| 6,394,314 | B1 * | 5/2002 | Sawhney | A47J 37/1271 210/244 |
| 6,582,407 | B1 * | 6/2003 | Lo | A61M 5/5013 604/110 |
| 6,837,399 | B1 * | 1/2005 | Wagner | A61C 5/064 222/1 |
| 6,936,033 | B2 * | 8/2005 | McIntosh | A61B 17/00491 604/191 |
| 6,972,005 | B2 | 12/2005 | Boehm, Jr. et al. | |
| 7,081,103 | B2 | 7/2006 | Epstein et al. | |
| 7,367,475 | B2 * | 5/2008 | Horth | A61C 5/062 222/145.5 |
| 8,251,915 | B2 * | 8/2012 | Dunn | 600/564 |
| 8,419,722 | B2 * | 4/2013 | Richards et al. | 606/27 |
| 2004/0106196 | A1 * | 6/2004 | Fraser | C12N 5/0667 435/366 |
| 2004/0138685 | A1 * | 7/2004 | Clague | A61B 17/12 606/167 |
| 2004/0257908 | A1 * | 12/2004 | Breuker et al. | 366/162.5 |
| 2005/0149092 | A1 * | 7/2005 | Dunn | 606/185 |
| 2005/0165345 | A1 * | 7/2005 | Laufer et al. | 604/26 |
| 2005/0177100 | A1 | 8/2005 | Harper et al. | |
| 2006/0014440 | A1 * | 1/2006 | Sogaro | A61C 9/0026 439/652 |
| 2006/0100587 | A1 * | 5/2006 | Bertron | A61M 5/284 604/191 |
| 2006/0100590 | A1 | 5/2006 | Thorne, Jr. et al. | |
| 2007/0191781 | A1 * | 8/2007 | Richards et al. | 604/191 |
| 2007/0224173 | A1 | 9/2007 | Koullick et al. | |
| 2007/0274960 | A1 * | 11/2007 | Harman et al. | 424/93.7 |
| 2008/0014181 | A1 | 1/2008 | Ariff et al. | |
| 2008/0125782 | A1 * | 5/2008 | Rydell et al. | 606/79 |
| 2008/0243028 | A1 * | 10/2008 | Howard | A61B 17/1635 600/565 |
| 2008/0249552 | A1 * | 10/2008 | Eliachar et al. | 606/171 |
| 2008/0287987 | A1 * | 11/2008 | Boyden | A61B 17/068 606/214 |
| 2008/0319417 | A1 | 12/2008 | Quijano et al. | |
| 2009/0018496 | A1 | 1/2009 | Harper et al. | |
| 2009/0024085 | A1 * | 1/2009 | To | A61B 17/32075 604/95.01 |
| 2009/0048558 | A1 * | 2/2009 | Del Vecchio | A61J 1/2096 604/22 |
| 2009/0240208 | A1 * | 9/2009 | Cowan | A61M 5/329 604/190 |
| 2010/0101454 | A1 * | 4/2010 | Wendelin | B01F 3/1221 106/243 |
| 2010/0256646 | A1 * | 10/2010 | Pinal et al. | 606/92 |
| 2011/0008299 | A1 * | 1/2011 | Koullick et al. | 424/93.7 |

OTHER PUBLICATIONS

Merriam Webster Online Dictionary. "Definition of Triturate." Accessed Dec. 18, 2015. http://www.merriam-webster.com/dictionary/triturating.*

Merriam Webster Online Dictionary. "Definition of Comminute." Accessed Dec. 18, 2015. http://www.merriam-webster.com/dictionary/comminution.*

* cited by examiner

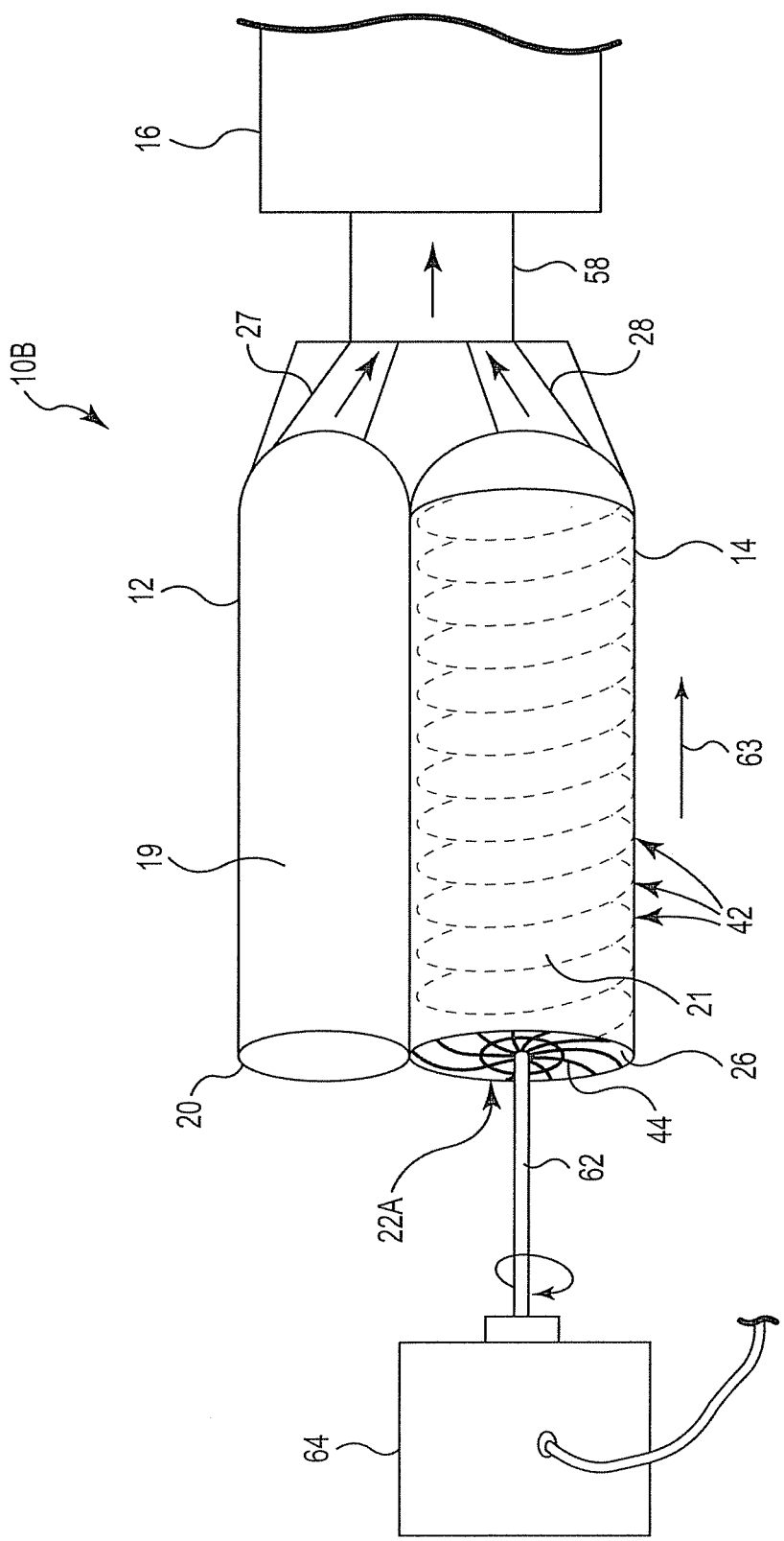

MULTI-CHAMBER CELLULAR MIXING AND DELIVERY SYSTEM AND METHOD

This application claims the benefit from International Application No. PCT/US2010/041508, which was filed on Jul. 9, 2010, which in turns claims priority under 35 U.S.C. § 119(e) to Provisional Application No. 61/224,363, filed Jul. 9, 2009, which are both incorporated herein by reference in their entireties.

FIELD OF THE INVENTION

The present invention relates generally to syringe systems and, more particularly, to a multi-chamber delivery system adapted to inject damaged or defective target tissue, such as the corpora of the male penis, with a cellular mixture.

BACKGROUND OF THE INVENTION

Erectile dysfunction (ED) is believed to affect more than ninety million men in the United States and Europe, with seventeen million presenting with severe conditions that greatly interfere with the ability to initiate and maintain erections. ED may arise from a number of causes. Age brings on a lack of arterial elasticity in vessels supplying blood to erectile tissues. Damage to nerves necessary for initiating and sustaining erections brought on by chronic conditions (such as diabetes) or by injury can lead to dysfunction. A significant cause of nerve damage comes from injury that occurs during prostate surgeries, especially radical prostatectomies. Although new surgical procedures have been introduced that conserve the nerves in this region, a majority of men who undergo such procedures can still expect some degree of post operative ED.

A number of oral medications for treating ED have entered the marketplace in recent years, including VIAGRA, CIALIS and LEVITRA. These medications all provide significant relief to a large segment of men with ED. However, they each require that the medication be taken in advance of initiation of sexual activity and their effects may be delayed if ingested with food. Further, the effectiveness of such drugs can vary greatly from patient to patient, and the drugs even have been found ineffective in a large cross-section of patients.

Various treatments have also been tried in connection with ED, including administration of Prostaglandin E1 by injection into the cavernosum of the penis, by administration of a suppository into the urethra, and by topical administration. These approaches allow for less advance preparation, but are neither consistently effective nor desirable applications across patient populations, especially radical prostatectomy patients.

Surgical interventions are also available for addressing ED, especially where medications are ineffective or contraindicated. Penile implants of many different configurations are used to provide support for an erection. These implants are effective in restoring patient sexual satisfaction. Increasingly, these implants have been engineered to be completely concealed within the patient. However, implants may fail over time and replacement or total removal may be required potentially leaving the patient with no relief at all. In addition, penile implants are an end stage treatment, and it is often desirable to provide treatment earlier in the disease state. Thus, there is a desire to obtain a minimally invasive yet effective and durable solution to treat ED that can be used with minimal to no side effects. Current syringe and needle devices and systems are not adequate to inject, grind, filter and mix cell and adipose mixtures into the proper location.

In addition to ED, there is a need for alternative yet effective solutions to treat other damaged or defective tissues within the pelvic region of a patient (man or woman), including conditions such as male and female fecal and urinary incontinence, bladder pain, vaginal prolapse, and overall uterine health. Again, such a treatment can include injecting a cellular mixture in or around damaged or defective tissue.

SUMMARY OF THE INVENTION

A multi-chamber mixing and delivery system is provided herein to solve many of the problems inherent in conventional systems and methods for treating disorders, such as ED. The systems and methods of the present invention can include various components and elements to facilitate mixing, digesting, filtering, and injecting cellular mixtures, such as cells and autologous adipose tissue, into target tissue of a patient to treat ED, urinary and fecal incontinence, bladder pain, vaginal prolapse, and other pelvic health disorders.

For this therapy, cells may be injected into the penis alone or in combination with a scaffold material, such as adipose. One example is the injection of adipose-derived cells in combination with unprocessed adipose tissue where the tissue acts as a scaffold for the cells.

Injection of adipose derived cells in combination with unprocessed adipose tissue requires specialized accessories and/or injection tools that contain elements that mechanically grind or digest the tissue, filter the digested tissue, and mix the cells and tissue. Delivery of the cell/tissue mixture may also utilize multi-chamber syringes and needles of specific length to properly position the tip of the needle within the injection site.

BRIEF DESCRIPTION OF THE DRAWINGS

FIG. 4 is a diagram illustrating an exemplary grinder element in accordance with the present invention incorporated into the system of FIG. 3.

DETAILED DESCRIPTION OF THE INVENTION

Referring generally to FIGS. 1-7, various embodiments of multi-chamber mixing and delivery systems 10 are shown. As will be discussed in further detail to follow, the systems 10 can include various components and elements to facilitate mixing, digesting/grinding, filtering, and injecting cellular mixtures, such as cells and autologous adipose tissue or scaffolding material, into target tissue of a patient to treat ED, urinary and fecal incontinence, bladder pain, vaginal prolapse, and other pelvic health disorders. The various components of the systems 10 can be constructed of materials such as polymers, metals, and other like materials compatible for use with such injection systems and methods.

The various systems 10 set forth herein will be described with reference to the treatment of ED. With such a treatment application, cell and adipose mixtures may be injected into the corpora in a manner that assists in distributing and retaining the cellular mixture within the corpora for a period of time, such as a period of several minutes. Proper distribution and cell retention is promoted by driving the cellular mixture into the larger sinusoid spaces of the mid-corpora. Before, during, or after injection of the cellular mixture into the corpora of the male penis, a vacuum (e.g., a vacuum erection device) or other like device can be implemented to further promote the influx of blood into the penis to increase distribution and cellular viability through increased oxygenation of the tissues. Various devices, drugs, and known means can also be implemented to induce an erection before, during, or after the injection to promote blood flow in the penis.

Although the systems 10 of the present invention are described herein as being used to treat ED, workers skilled in the art will appreciate that the systems 10 may be used for the cellular treatment of various other disorders without departing from the intended scope of the present invention. Thus, the treatment of ED is described merely for purposes of example and not limitation.

As will further be appreciated by those skilled in the art, the to novel features of the systems 10 and corresponding methods detailed herein may be incorporated into any suitable known injection and syringe system and method, including but not limited to those disclosed in U.S. Patent Publication Nos. 2005/0177100, 2006/0100590, 2007/0224173, 2008/0014181, 2008/0287879, and 2009/0018496; U.S. Pat. No. 7,101,354; and PCT International Patent Publication No. WO2008/091251. Accordingly, the above-identified disclosures are incorporated herein by reference in their entirety.

Figure 1:
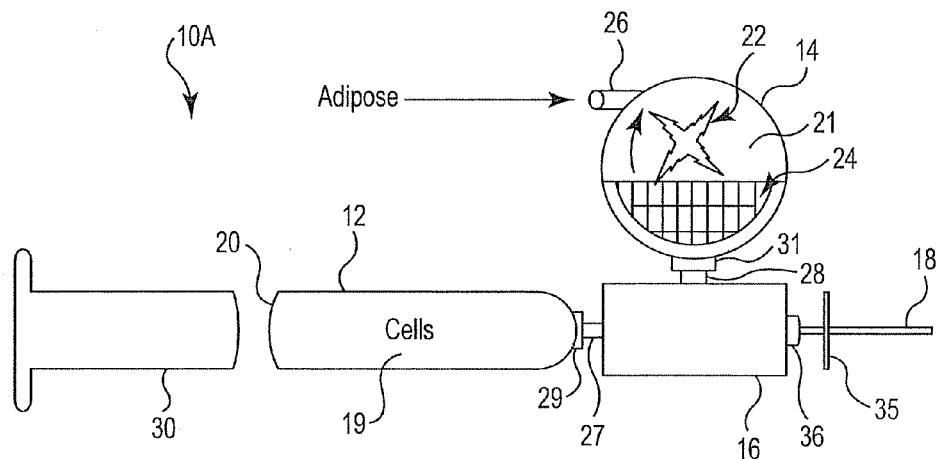
FIG. 1 is a diagram illustrating a first exemplary embodiment of a multi-chamber mixing and delivery system in accordance with the present invention.

FIG. 1 is a diagram illustrating a first exemplary embodiment of a multi-chamber mixing and delivery system 10A in accordance with the present invention. As depicted in FIG. 1, the system 10A can include a first syringe chamber 12, a second syringe chamber 14, a mixing element 16, and an injection needle 18. The first syringe chamber 12 includes a lumen or interior portion 19 defined therethrough and can further include an inlet port or opening 20 for accessing the interior portion 19. The second syringe chamber 14 also includes an interior portion 21 having a tissue reduction or grinder element 22 and a mesh or filter element 24 disposed therein. The second syringe chamber 14 may further include an inlet port or opening 26 for accessing the interior portion 21 of the chamber. In the exemplary embodiment described herein, the first syringe chamber 12 is generally adapted to receive and advance various cells, while the second syringe chamber 14 is adapted to receive and advance scaffolding tissues, such as adipose tissue.

As further illustrated in FIG. 1, the first syringe chamber 12 may include a distal outlet port 27 that is structured to pass cells from the interior portion 19 into the mixing element 16. Similarly, the second syringe chamber 14 may include a distal outlet port 28 that is structured to pass filtered adipose tissue from the interior portion 21 into the mixing element 16. As will be appreciated by those skilled in the art, the outlet ports 27 and 28 may be controlled by valve elements 29 and 31, respectively, that are operably coupled to or disposed within the outlet ports. Any suitable valves may be used, including but not limited to valves that are mechanically, electrically, or pneumatically controlled. In one exemplary embodiment, the valves may comprise a slit-type valve that is actuated by a differential pressure or force that is greater than the required displacement pressure or force of the valve. For example, the displacement pressure or force may be applied through actuation of a plunger device.

It is noted that adipose (i.e., fat) tissue includes or yields a high number of desirable cell types, including stem cells. The adipose tissue can come from anywhere in the body. In one embodiment, the adipose tissue is obtained from the abdominal area of the patient. Other common areas may include the thigh and back area of the patient. Once the adipose is obtained, half can be washed and then set aside for processing and injection via the second syringe chamber 14, while the other half can be processed into cells for injection via the first syringe chamber 12. The heterogeneous cell mixture that is disposed within the first syringe chamber 12 and derived from fat can include endothelial cells, endothelial precursors and progenitors, mesenchymal stem cells, vascular smooth muscle cells, fibroblasts, pericytes, macrophages, and the like. This heterogeneous cell mixture may be obtained using any suitable cell processing or separating method known to those skilled in the art.

Prior to advancement into the mixing element 16, the adipose tissue within the second syringe chamber 14 can be reduced in size at the grinder element 22, and subsequently passed through the filter element 24. As such, adipose tissue of varying sizes and shapes can be reduced to a desirable and predefined dimension before passing through for mixing with the cells of the first syringe chamber 12 at the mixing element 16.

As will be appreciated by those skilled in the art, any suitable tissue reduction or grinding element may be used including, but not limited to, a mechanical grinder, mincer, chopper, masher, or mortar and pestle. Optionally, the interior portion 21 may include a rough or abrasive surface to enhance the grinding process. The rough or abrasive surface may be formed directly into the surface itself, or may be applied to the surface as a surface coating. In one exemplary embodiment as illustrated in FIG. 1, the grinder element 22 can include a plurality of rotating blades or members. The rotating blades may either remain in a fixed location or move in various directions throughout the chamber during operation, and may be driven mechanically, manually, or electrically. For example, any suitable type of motor that is operable to rotate a shaft coupled to the grinder element 22, such as a stepper motor, may be incorporated into the systems of the present invention. Control of the motor may be automated or based on user input. Alternatively, simpler embodiments may involve the manual rotation of the shaft by the user, such as by manually rotating a handle coupled to the shaft.

As will further be appreciated by those skilled in the art, any suitable filtering means may be used that is structured to separate suitably sized adipose particles from other adipose particles or tissues that are too large for the injection. The filter element 24 may be either a static device or a dynamic device. In one exemplary embodiment, the filter element 24 may comprise a plastic, rubber, or metal cage-like element having a plurality of apertures defining the maximum acceptable particle size. In another exemplary embodiment, the filter may be formed from a suitable, porous cloth material, such as cheesecloth. The filter may take on any suitable shape or configuration such as a substantially flat plate or a rounded "bowl" like configuration. As an alternative to the illustrated filter element 24, a centrifuge that is configured to spin the adipose tissue may be used to filter out the desired particles.

The ideal or predefined dimensional requirements for the adipose particles can vary greatly depending on the attributes and characteristics of the defective or damaged target tissue, or the application to which the injection treatment is directed. However, for various exemplary embodiments a desirable size for the adipose particles may be approximately 1 mm or smaller, such as for treatments directed to injecting the cellular mixture into the mid-corpora of the penis where the sinusoid spaces are generally the largest. Thus, in one exemplary embodiment, the filter element 24 may be structure to exclude adipose particles that are greater than about 1 mm. Other suitably sized filter elements can be employed depending on the particular treatment site and needs as will be appreciated by those skilled in the art.

Figure 2A:
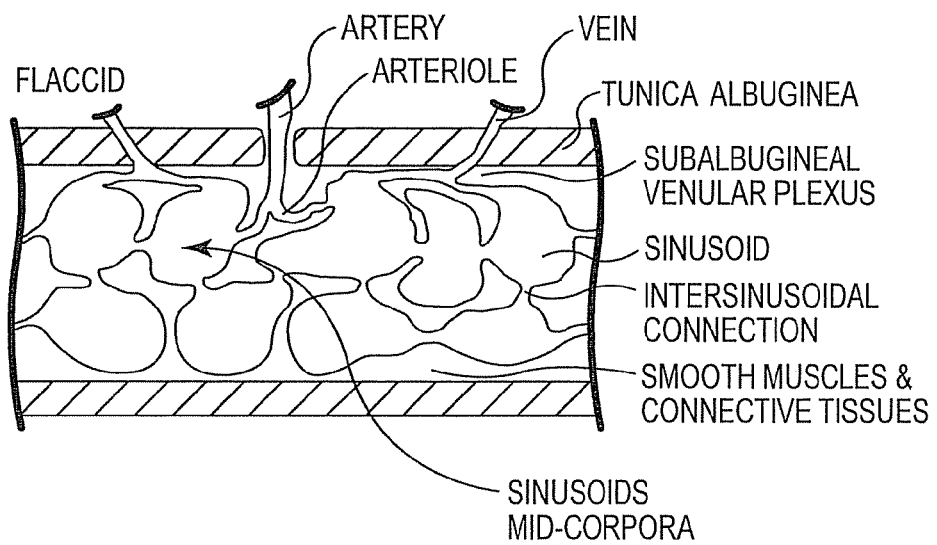
FIGS. 2A and 2B are diagrams of the male penis, flaccid and erect, illustrating various anatomical areas including the mid-corpora sinusoids (Fournier, Juenemann, Lue, and Tanagho. Journal of Urology, 137:163-167, 1987).
Figure 2B:
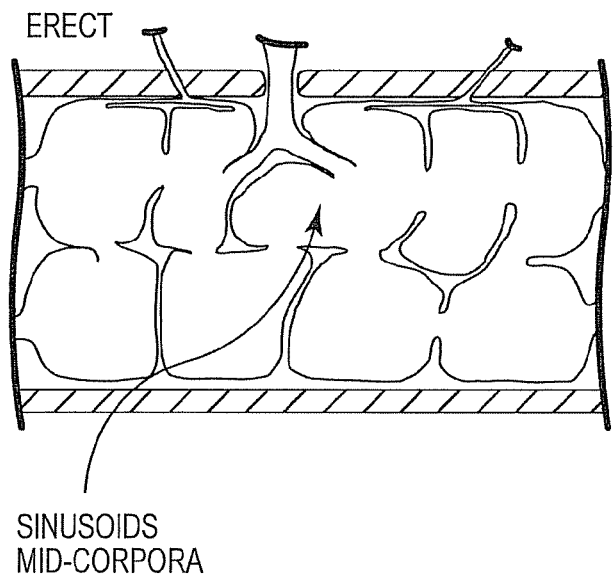

With reference to FIGS. 2A and 2B, diagrams of the male penis in both a flaccid and erect state are shown illustrating various anatomical areas of the penis, including the mid-corpora sinusoids (Fournier, Juenemann, Lue, and Tanagho. Journal of Urology, 137:163-167, 1987). Venous outflow originates in tiny venules leading from the peripheral sinusoids immediately beneath the tunica. Accordingly, the adipose particles are preferably reduced in size within the second syringe chamber 14 such that upon injection they remain in the larger mid-corpora, generally preventing the particles from travelling to the smaller peripheral sinusoids of the penis and thereby reducing the risk of a fat embolism.

Turning again to FIG. 1, the mixing element 16 is in fluid and operative communication with the first syringe chamber 12 via the outlet port 27, the second syringe chamber 14 via the outlet port 28, and the needle 18 via a mixing element output 36. The mixing element 16 assists in ensuring that the cellular mixture does not separate prior to injection into the treatment site. Any suitable components, structures, and techniques known to those skilled in the art can be used to mix and retain the cellular mixture of adipose and cells received from the first and second syringe chambers 12 and 14 into the mixing element 16 prior to injection into the target tissue through the needle 18. Examples of such mixing elements will be described in further detail to follow. In addition, a controlled dispensing component or element can be provided at or in communication with the mixing element, or other components of the system 10A, to deliver a certain or predefined number of cells, cell volume, or rate of cells through the needle 18 and to the target tissue site.

As illustrated in FIG. 1, one or more plunger devices 30 can be included to facilitate advancement of the cells, adipose tissue, and cellular mixture through the system 10A and out the injection needle 18. Although only one such plunger device 30 associated with the first syringe chamber 12 is shown, those skilled in the art will appreciate that another plunger device 30 may be associated with the second syringe chamber 14. Alternatively, various other means for advancing cells, adipose tissue, and cellular mixture through the system 10A may be employed without departing from the intended scope of the present invention.

Optionally, the needle 18 can include a stop 35 or other selectively adjustable structure to ensure that the needle travels to a desired or predetermined depth within the target tissue. In addition to the stop 35 being adjustable, it may also be designed such that it is completely removable from the injection needle 18 if desired. In one exemplary embodiment, the stop 35 can be sized, such as a flange, to abut against the outside of the target tissue so that only the remaining length from the stop to the distal end of the needle 18 will penetrate tissue.

Further, various known attachment and sealing components, structures, and techniques can be used to interlock or connect the various components of the syringe system 10A. Such components may include, but are not limited to, luer taper fittings and rubber septa. As appreciated by those skilled in the art, luer taper fittings are a class of fluid fittings used for making leak-free connections between a male taper fitting and a mating female fitting. With reference to the system 10A of FIG. 1, the outlet port 27 may comprise the male taper fitting while the female fitting may be coupled to or form part of the mixing element 16. Luer taper fittings are typically structured as either a luer lock connector or a luer press-fit connector. Generally speaking, luer lock connectors comprise a tabbed hub on a female fitting which screws onto a threaded sleeve of a male fitting. Luer taper press-fit connectors comprise a male sleeve fitting that is pressed into a female fitting. Rather than using threads, the male and female fittings are held together by the force of friction. As further appreciated by those skilled in the art, rubber septa are stopper-like elements that are structured to provide a fluid and/or air-tight seal between two adjoining components. Typically, rubber septa are designed such that they may be easily pierced by a sharp needle or cannula to provide a pathway therethrough.

Providing luer taper fittings between the first and second syringe chambers 12 and 14 and the mixing element 16 allows for separation of the components and enables a user to remove one or more of the components easily and quickly. For example, after delivering the adipose tissue through the second syringe chamber 14 and into the mixing element 16, the second syringe chamber 14 may be removed from the mixing element 16 and the luer fitting "capped."

Figure 3:
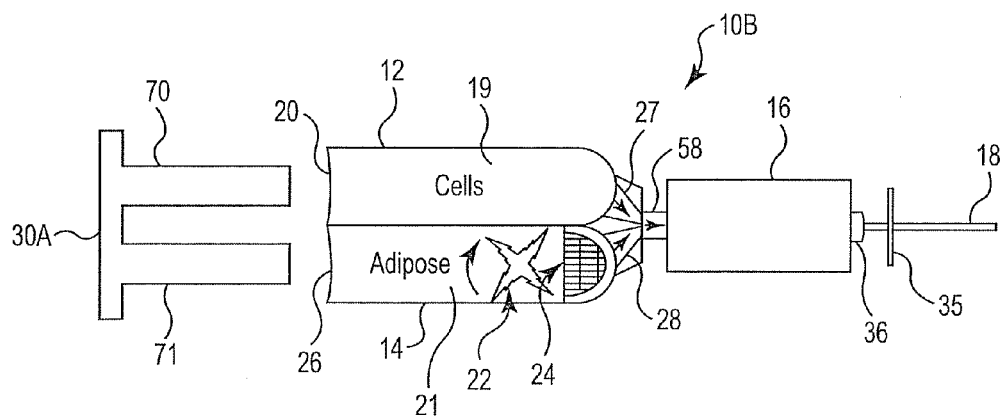
FIG. 3 is a diagram illustrating a second exemplary embodiment of a multi-chamber mixing and delivery system in accordance with the present invention.

FIG. 3 is a diagram illustrating a second exemplary embodiment of a multi-chamber mixing and delivery system 10B in accordance with the present invention. As depicted in FIG. 3, the system 10B is generally similar to the system 10A previously described. However, the first and second syringe chambers 12 and 14 are disposed in a generally parallel or adjacent configuration. The first and second syringe chambers 12 and 14 may be separate components that are coupled together along their outer surfaces to form a single syringe assembly. Alternatively, the first and second syringe chambers 12 and 14 may be formed as two distinct chambers extending side-by-side within a main body (i.e., a "dual-chamber" syringe). As discussed in detail above with reference to the system 10A, the second syringe chamber 14 can be adapted for receiving, grinding, and mixing the adipose particles or tissue, with the mixing element 16 in fluid and operative communication with the first and second syringe chambers 12 and 14.

The first and second syringe chambers 12 and 14 may include separate, independently operable plunger devices to facilitate advancement of the cells, adipose tissue, and cellular mixture through the system 10B and out the injection needle 18. Alternatively, as shown in FIG. 3, a "dual" plunger device 30A may be provided that includes a first plunger portion 70 that is structured to be received within the first syringe chamber 12 and a second plunger portion 71 that is structured to be received within the second syringe chamber 14. The dual plunger device 30A is operable to advance cells and adipose tissue simultaneously through the first and second syringe chambers 12 and 14.

As will be appreciated by those skilled in the art, the outlet port 27 of the first syringe chamber 12 and the outlet port 28 of the second syringe chamber 14 may be fluidly coupled to an inlet port 58 of the mixing element 16. Alternatively, the mixing element 16 may include a second inlet port (not shown) such that the cells and adipose tissue from the chambers do not converge and begin to mix until they are within the interior of the mixing element 16.

As previously discussed, the filter element 24 can be disposed within the second syringe chamber 14 such that only the desired size adipose particles and mixture of cells are allowed to travel into the mixing element 16 that is provided in operative and fluid communication with the first and second syringe chambers 12 and 14. Once again, various plungers, stops, attachment, and sealing components as disclosed herein or known to those skilled in the art can be employed with the system 10B of FIG. 3 in a manner similar to that described with reference to the system 10A of FIG. 1. In addition, a controlled dispensing component or element can be provided at or in communication with the mixing element, or other components of the system 10B, to deliver a certain or predefined number of cells, cell volume, or rate of cells to the target tissue site.

Figure 5:
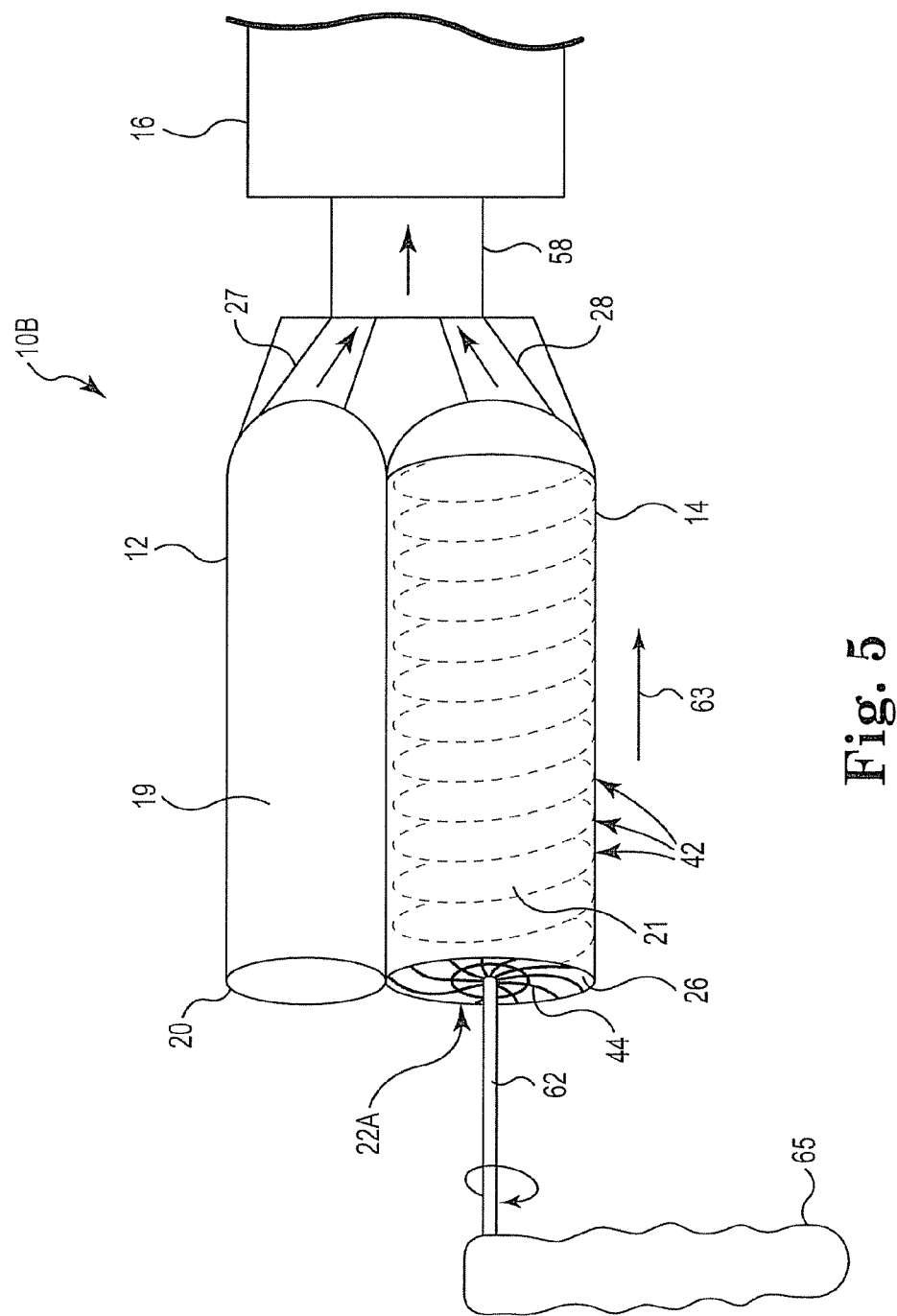
FIG. 5 is a diagram illustrating the grinder element of FIG. 4 with a manual, rotatable handle for powering the grinder element.

FIG. 4 is a diagram illustrating an alternative grinder element 22A in accordance with the present invention incorporated into the system 10B of FIG. 3. As depicted in FIG. 4, the grinder element 22A may comprise a plurality of threads 42 on the interior portion 21 of the syringe chamber 14 and a blade assembly 44 that is operable to drive and mechanically digest or blend the adipose tissue into smaller particles. The blade assembly 44 may be operably coupled to a shaft 62 that is structured to rotate the blade assembly 44 and drive the assembly along the threads 42 in the direction indicated by arrow 63 to grind the adipose tissue and force the tissue particles through a suitable filter element as discussed above. The shaft 62 and attached blade assembly 44 may be rotated using any suitable rotations means, such as a drive motor 64 as depicted in FIG. 4. Operation of the drive motor 64 may be controlled by the user, such as with an "on/off" switch, or the drive motor 64 may be programmed for automated operation (i.e., duration, speed, etc.) without the need for monitoring by the user. In one exemplary alternative embodiment, the shaft 62 and attached blade assembly 44 may be manually rotated with a suitable handle element 65 as illustrated in FIG. 5.

Figure 6A:
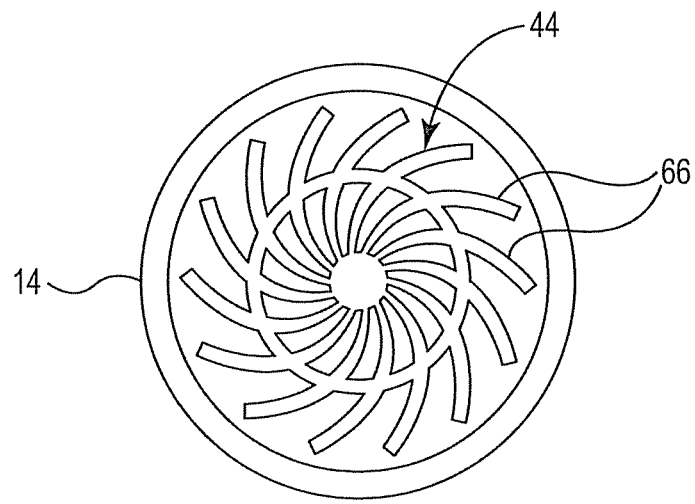
FIG. 6A is a cross-sectional view a syringe chamber with a blade assembly of the FIG. 3 grinder element disposed therein.

FIG. 6A is a cross-sectional view of the second syringe chamber 14 with the blade assembly 44 disposed therein. As shown in FIG. 6A, the blade assembly 44 includes a plurality of blade elements 66 arcing from a center connector and having sharp, knife-like edges for grinding tissue. Those skilled in the art will appreciate that numerous other blade configurations are possible, such as blades that extend radially outward from a center connector without arcing or curving.

Figure 6B:
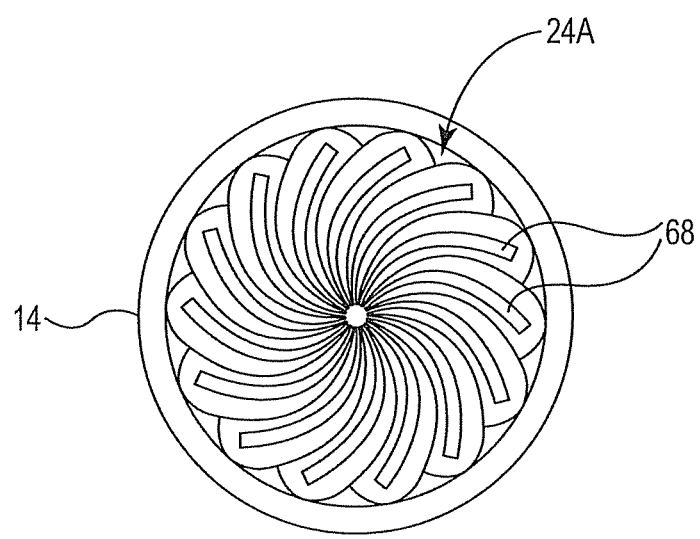
FIG. 6B is a cross-sectional view of a syringe chamber with an exemplary filter element disposed at a distal end therein.

FIG. 6B is a cross-sectional view of the second syringe chamber 14 with an exemplary filter element 24A disposed at a distal end therein. As shown in FIG. 6B, the filter element 24A includes a plurality of arcing slots 68 equal in number to the number of blade elements 66 of the blade assembly 44. The filter element 24A is structured to filter the blended adipose so that only appropriately sized particles pass into the mixing element that is in operative and fluid communication with the chamber 14. As will be appreciated by those skilled in the art, various other filter designs are also possible, such as filter slots that extend radially outward from a center region of the filter without arcing or curving.

Figure 7:
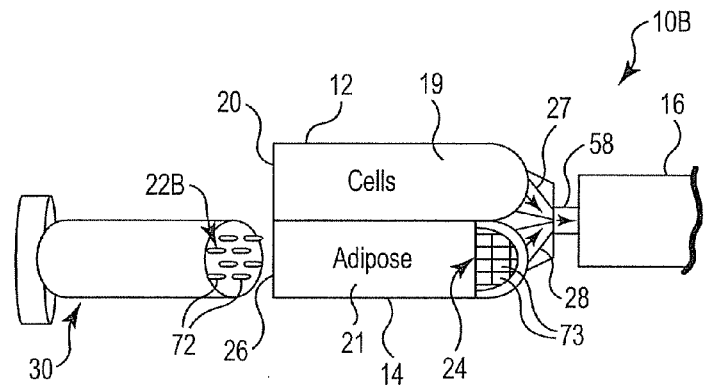
FIG. 7 is a diagram illustrating another alternative grinder element in accordance with the present invention incorporated into the system of FIG. 3.

FIG. 7 is a diagram illustrating another alternative grinder element 22B in accordance with the present invention incorporated into the system 10B of FIG. 3. As depicted in FIG. 7, the grinder element 22B may comprise a plurality of protruding "punch" elements 72 on a distal end of a plunger device 30 that are structured to be received within a plurality of corresponding holes 73 in the mesh or filter element 24 near the outlet port 28. The plunger device 30 is generally configured for travel through at least a portion of the interior portion 21 of the second syringe chamber 14. As the plunger device 30 approaches the mesh or filter element 24, the adipose tissue is ground up and digested into particles of a desirable size as it is pressed through the holes 73. Thus, the alternative grinder element 22B functions similar to a "punch press" or "garlic press" to reduce the size of the adipose tissue particles. Optionally, the holes 73 may have one or more sharp edges to enhance the grinding effect. Once the plunger device 30 is depressed, the digested adipose tissue and cells are delivered to the mixing element 16 and subsequently to the needle 18 as previously described.

Figure 8:
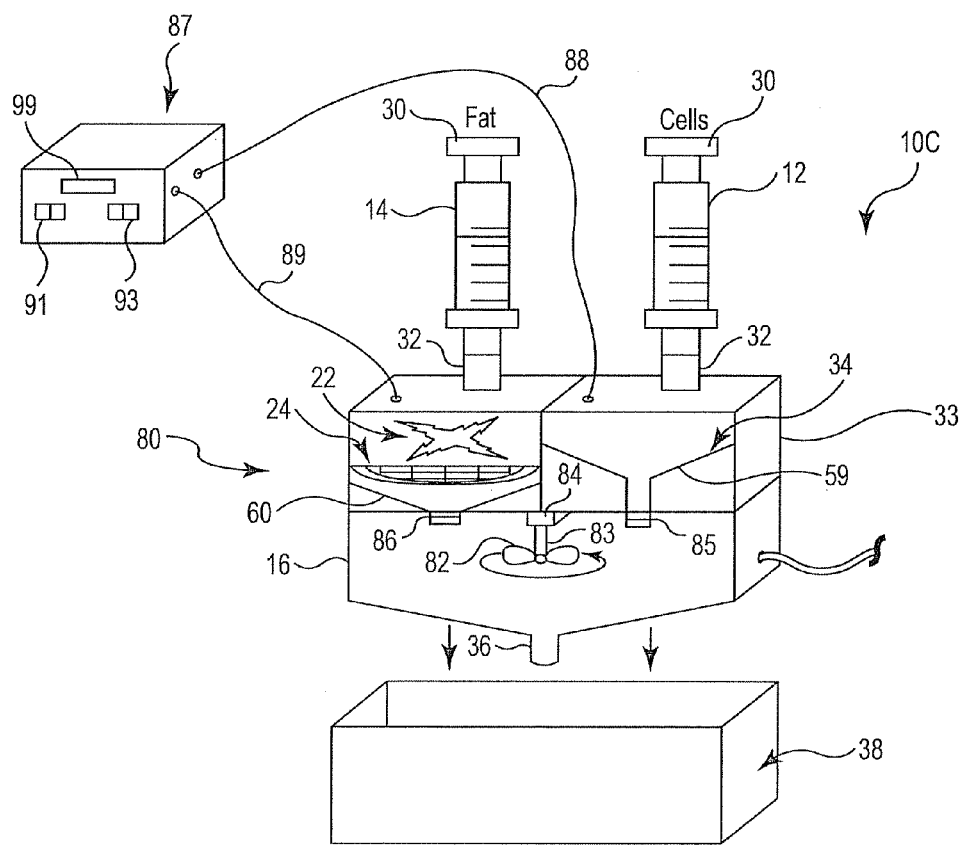
FIG. 8 is a diagram illustrating a third exemplary embodiment of a multi-chamber mixing and delivery system in accordance with the is present invention having a concentration chamber operably coupled to a mixing element.

FIG. 8 is a diagram illustrating a third exemplary embodiment of a multi-chamber mixing and delivery system 10C in accordance with the present invention. As depicted in FIG. 8, the system 10C includes a mixing platform assembly 80 that comprises the mixing element 16 and a cell concentration chamber 33 that contains the grinder element 22 and filter element 24. Thus, as will be appreciated by those skilled in the art in view of the system 10C embodiment, the grinder element 22 and the filter element 24 (or alternatively only the filter element 24) may be removed from the second syringe chamber 14 without departing from the intended scope of the present invention.

Particularly, the first and second syringe chambers 12 and 14 are provided in operative and fluid communication with the cell concentration chamber 33, which in turn is in fluid communication with the mixing element 16. The first and second syringe chambers 12 and 14 can include plunger devices 30 adapted to travel within at least a portion of the respective syringe chambers to drive the cells and adipose tissue through to the cell concentration chamber 33. Various means other than a plunger may also be employed to drive the cells and/or adipose tissue through the cell concentration chamber 33 as will be appreciated by those skilled in the art.

Once the adipose tissue is within the cell concentration chamber 33, it may be digested or ground down by the grinder element 22 and filtered through the filter element 24 for controlled volume dispensing into the mixing element 16. Likewise, the cells are driven from the first syringe chamber 12 into a distinct portion of the cell concentration chamber 33 for controlled volume dispensing into the mixing element 16. As illustrated in FIG. 8, the cells and adipose tissue may be collected and directed toward the mixing element 16 with collection elements such as first and second funnels 59 and 60. The first and second funnels 59 and 60 may include first and second control valves 85 and 86, respectively, for controlling various factors such as the volume of material (i.e., cells or adipose particles) that is passed through the cell concentration chamber 33 and into the mixing element 16 and that rate at which the material is passed.

In one exemplary method of operation, the first and second control valves 85 and 86 are set to the desired volumes with a manual adjustment means. Alternatively, a controller 87 may be operably coupled to the first and second control valves 85 and 86 via corresponding first and second transmission lines 88 and 89. The controller 87 may include a first input 91 for inputting the desired final volume of the mixture, a second input 93 for inputting the desired ratio of cells to fat within the mixture, and a display 99 for displaying the values input by the user. During operation, the controller 87 is operable to control the first and second control valves 85 and 86 based upon the user input to automatically dispense the correct volume of material from each of the syringe chambers. For example, if a 10 cc final adipose and cell cocktail mixture with a 1:1 ratio of cells to fat is desired, the user may input these parameters into the controller 87 using the first and second inputs 91 and 93 and 5 cc would automatically be dispensed from the portion of the cell concentration chamber 33 associated with the first syringe chamber 12, and another 5 cc would be automatically dispensed from the portion of the cell concentration chamber 33 associated with the second syringe chamber 14.

Once the cells and adipose tissue particles are within the mixing element 16, the materials are then mixed in preparation for delivery through the outlet 36. Those skilled in the art will appreciate that any mixing element that is capable of providing a continuous, vortex-like motion may be used to mix the adipose and cell cocktail. As shown in FIG. 8, one exemplary mixing element 16 may include a rotatable propeller member 82 that is coupled to a shaft 83 extending into the interior of the mixing element 16. As the propeller member rotates, the cells and adipose tissue are "swirled" together in order to create the desired mixture. The propeller member 82 may be powered in any suitable manner, such as with a battery or electrically powered motor 84 as shown in FIG. 8.

In order to retrieve the mixed adipose and cell cocktail, the mixing element 16 may be lifted off of the base 38 in order to reveal the outlet 36 through which the mixture can be drawn. As will be appreciate by those skilled in the art, the outlet 36 can be adapted for operative fluid communication with an injection delivery device, such as the needle 18 previously described. The outlet 36 may include a suitable sealing element, such as a rubber septum, to ensure that the mixture does not leak from the mixing element 16.

As further illustrated in FIG. 8, various luer locks 32 or other known connection devices and structures can be used to selectively interconnect the various system components. Again, various plungers, stops, and attachment and sealing components as disclosed herein or known to those skilled in the art can also be employed with this embodiment.

Figure 9:
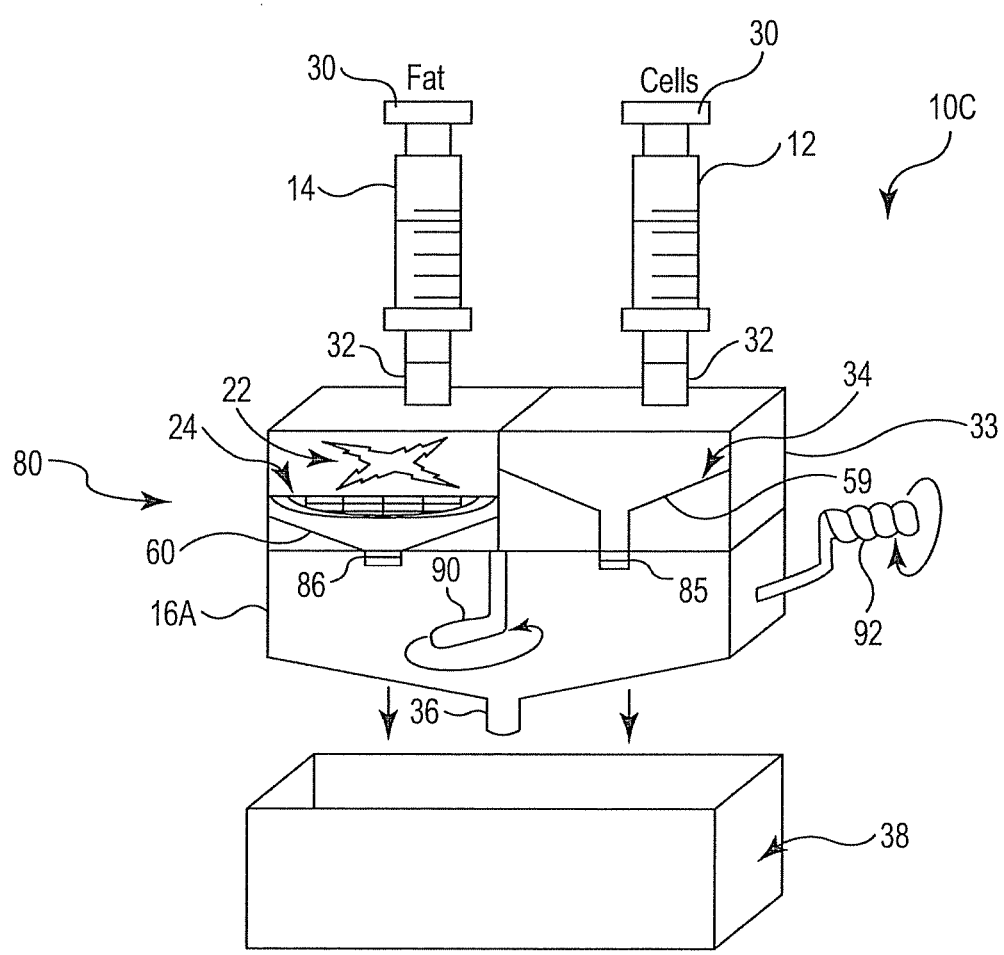
FIG. 9 is a diagram illustrating an alternative mixing element in accordance with the present invention incorporated into the system of FIG. 8.

FIG. 9 is a diagram illustrating an alternative mixing element 16A in accordance with the present invention incorporated into the system 10C of FIG. 8. As depicted in FIG. 9, the mixing element 16A includes a rotatable paddle member 90 that extends into the interior chamber of the mixing element. As the paddle member rotates, the cells and adipose tissue are "swirled" together in order to create the desired mixture. The paddle member 90 may be powered in any suitable manner, such as with a rotatable handle 92 that requires manual operation by the user as shown in FIG. 9.

Figure 10:
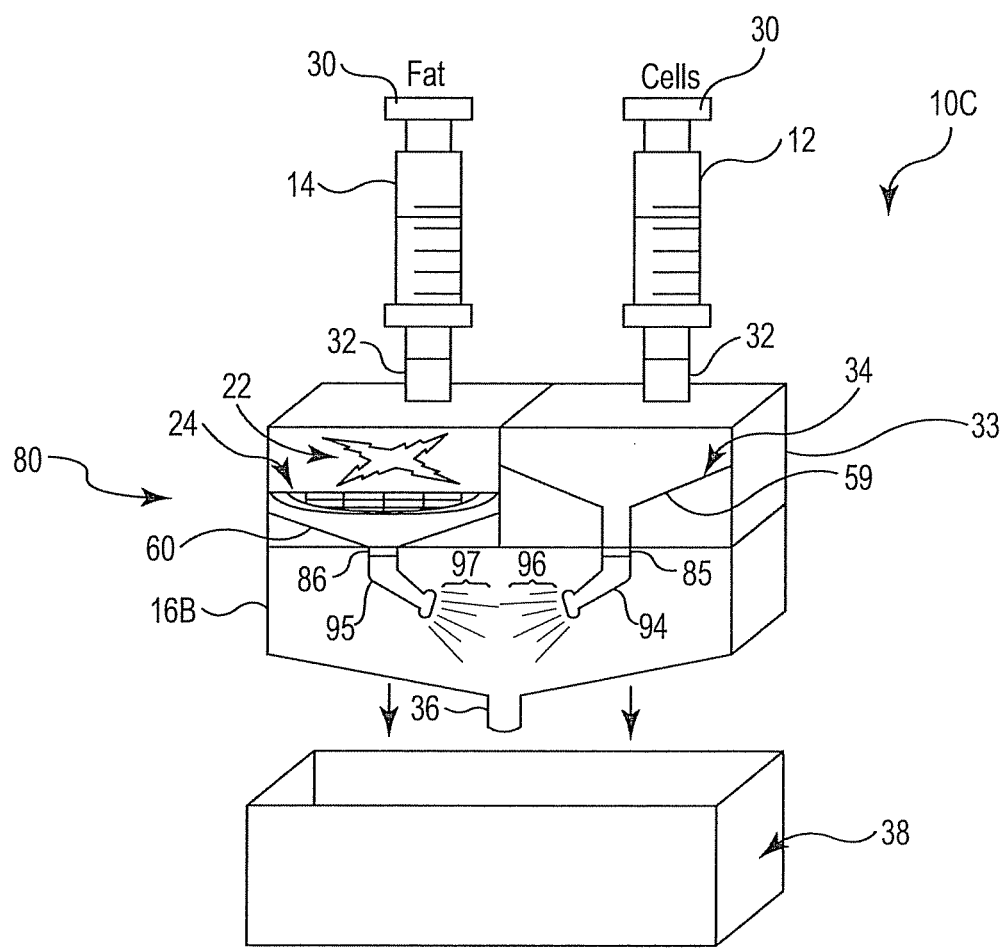
FIG. 10 is a diagram illustrating another alternative mixing element in accordance with the present invention incorporated into the system of FIG. 8.

FIG. 10 is a diagram illustrating another alternative mixing element 16B in accordance with the present invention incorporated into the system 10C of FIG. 8. As depicted in FIG. 10, the mixing element 16B includes a first spray nozzle 94 disposed at the output of the first funnel 59 and a second spray nozzle 95 disposed at the output of the second funnel 60. As the cells exit the first funnel 59, the first spray nozzle 94 creates a stream of cells 96 directed into the chamber of the mixing element. Similarly, as the adipose tissue particles exit the second funnel 60, the second spray nozzle 95 creates a stream of particles 97 directed into the chamber of the mixing element. As the streams 96 and 97 converge, the adipose and cell cocktail mixture is formed within the mixing element.

Figure 11:
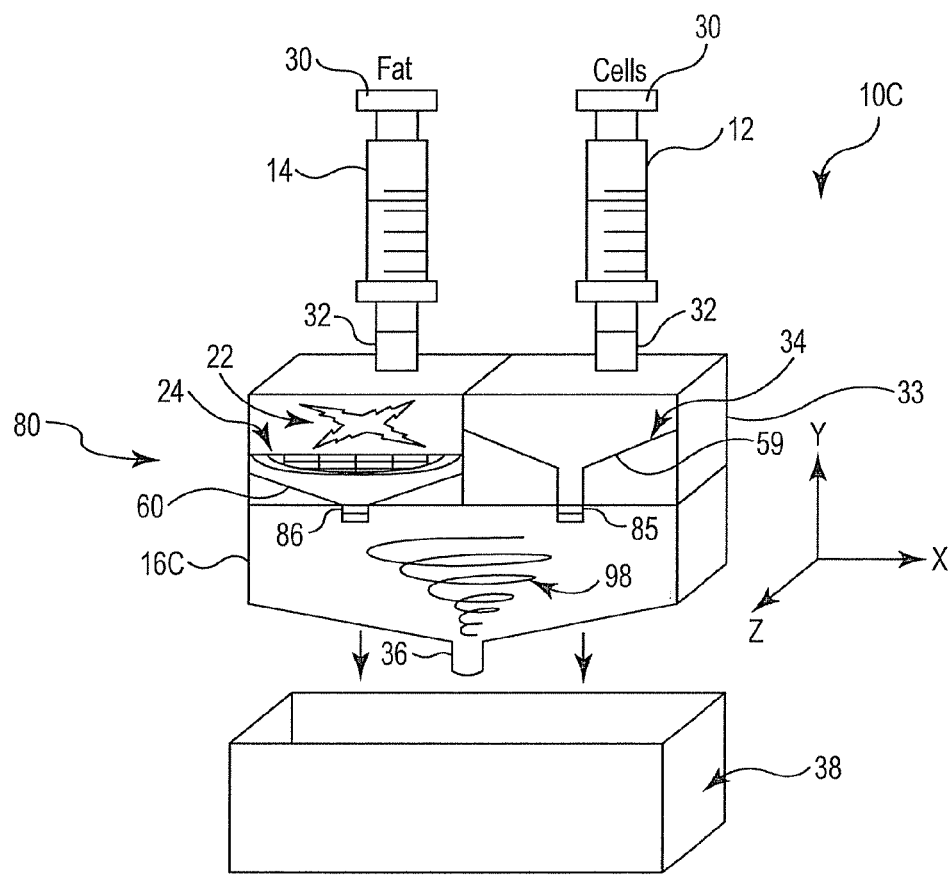
FIG. 11 is a diagram illustrating yet another alternative mixing element in accordance with the present invention incorporated into the system of FIG. 8.

FIG. 11 is a diagram illustrating yet another alternative mixing element 16C in accordance with the present invention incorporated into the system 10C of FIG. 8. As depicted in FIG. 11, the mixing element 16C does not include a mechanical mixing member as is present in the embodiments of FIGS. 8-10. Rather, the mixing element 16C is structured to be "shaken" in various directions, such as the directions defined by the illustrated x-, y-, and z-axes, to create a "vortex" 98 within the chamber of the mixing element for mixing the cells and adipose tissue. As will be appreciated by those skilled in the art, the shaking may occur manually through movement by the user or via any suitable shaking means, such as a mechanical shaker/mixer device of the type commonly used to mix paint in a hardware store.

Figure 12:
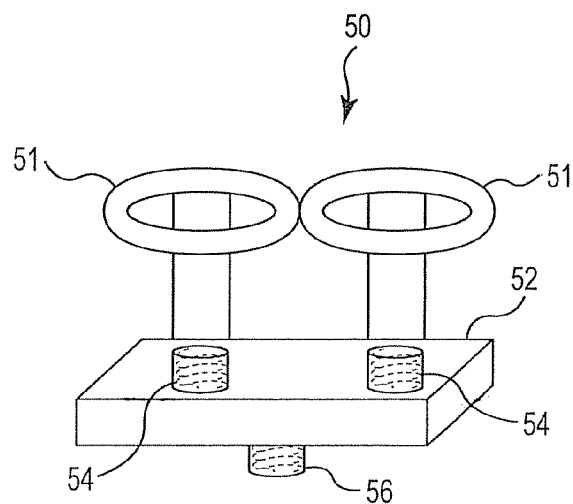
FIG. 12 is a diagram illustrating an exemplary syringe support assembly in accordance with the present invention that includes one or more syringe chamber holders structured for holding one or more syringe chambers together.

FIG. 12 is a diagram illustrating an exemplary syringe support assembly 50 in accordance with the present invention that includes one or more syringe chamber holders 51 that are structured for holding one or more syringe chambers together, such as the first and second syringe chambers 12 and 14. In one exemplary embodiment as illustrated in FIG. 12, the syringe chamber holders 51 may comprise circular rings or clamp members. The syringe support assembly 50 can also include a plurality of luer locks 54 or other connection means for connection to the syringe chambers. A base element 52 can include various devices, systems, and components to combine, blend, and/or mix the cellular constituents of the syringe chambers. Examples of such devices, systems, and components were described in detail above. The base element 52 may also include a connection portion 56 configured for communication with a needle device such that the cellular mixture from the base element 52 can be advanced for injection into the target tissue or site of the patient.

Figure 13:
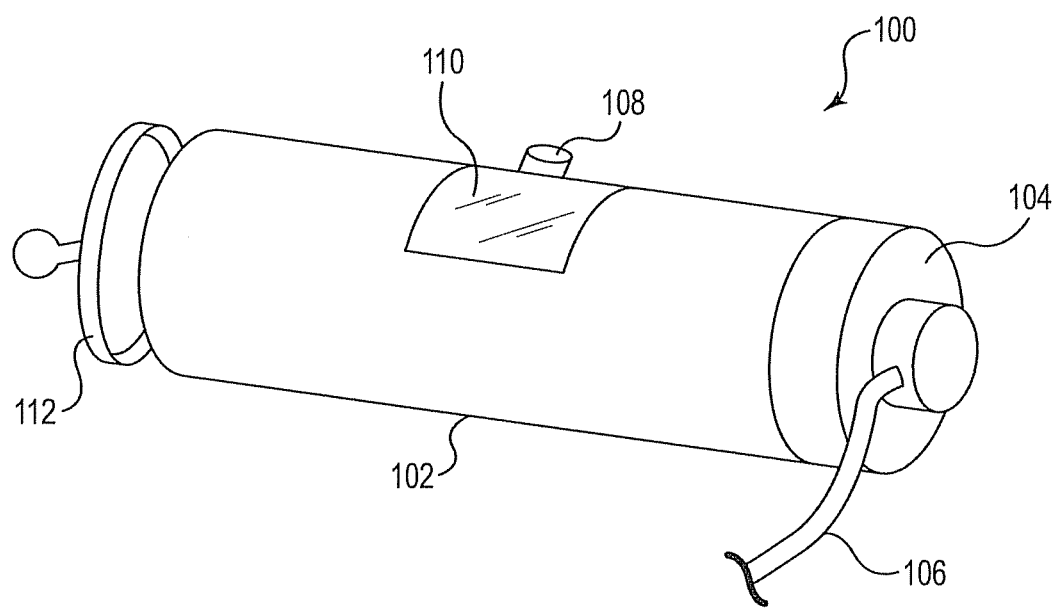
FIG. 13 is a diagram illustrating an exemplary vacuum erection device that is operable with the various mixing and delivery systems of the present invention to inject an adipose and cell cocktail mixture into the penis for the treatment of ED.

FIG. 13 is a diagram illustrating an exemplary vacuum erection device (VED) 100 that is operable with the various systems 10 described above to inject an adipose and cell cocktail mixture into the penis for the treatment of ED. As appreciated by those skilled in the art, VEDs are useful to control the rate of blood flow within the penis. The treatment of ED using cells may require that the cells injected into the corpora are distributed throughout and retained within the corpora for a period of time. Thus, in order to increase the retention and distribution of cells, an injection method that utilizes blood to drive cells into all of the sinusoid spaces of the corpora and to hold the cells in place for an extended period of time may be desired.

The VED 100 of the present invention generally includes a tubular main body 102, a cap member 104, a vacuum source 106 such as a hose fluidly coupled to a hand pump or similar device for creating a vacuum force within the main body 102, and an injection port 108. The injection port 108 may be structured and operable to enable use of the VED 100 immediately after injection rather than having to place the device after injection of the cellular cocktail with the injection system 10. The injection port 108 may include a suitable connection means, such as a luer lock and/or a rubber septum, to allow for the quick and easy connection of any of the injection systems 10 of the present invention to the VED 100. When a rubber septum or similar element is used, it is preferably formed from a material that may be easily punctured by a needle and that closes completely upon removal of the needle to maintain a vacuum pressure within the VED 100. Obviously, numerous other connection and/or sealing means may be used without departing from the intended scope of the present invention.

Optionally, a visualization window 110 may be incorporated into the main body 102 to accommodate more precise viewing of the injection area. Alternatively, the main body 102 of the VED 100 may be formed from a transparent material to allow the user to visualize the entire penis when positioned therein. The VED 100 may also include a ring member 112 that is structured for positioning at the base of the penis to assist within maintaining an erection for the desired period of time.

As will be appreciated by those skilled in the art, a variety of materials may be used to form portions or components of the systems 10, syringe support assembly 50, and VED 100 described above. Such materials may include nitinol, polymers, elastomers, thermoplastic elastomers, metals, ceramics, springs, wires, plastic tubing, and the like. Further, various components and devices disclosed herein for use with the systems 10 can include hinged and adjustable portions for selectively securing the systems 10 to the male penis in those embodiments being employed to treat ED. As such, ease of connection, decreased discomfort, and selective coupling of the systems 10 to the penis is promoted.

Obviously, numerous modifications and variations of the present invention are possible in light of the teachings herein. For example, the various embodiments of the system 10 in accordance with the present invention were described with reference to exemplary components such as the grinder elements, filter elements, mixing elements, and cell concentration elements merely for purposes of example and not limitation. Thus, it should be understood that the components illustrated herein may be interchanged between the various systems without departing from the intended scope of the present invention.

All patents, patent applications, and publications cited herein are hereby incorporated by reference in their entirety as if individually incorporated, and include those references incorporated within the identified patents, patent applications and publications.

Although the present invention has been described with reference to preferred embodiments, workers skilled in the art will recognize that changes may be made in form and detail without departing from the spirit and scope of the invention.

What is claimed is:

1. A multi-chamber mixing and injection system, the system comprising:
   a first chamber adapted to receive a cellular matter;
   a second chamber adapted to receive adipose tissue;
   a tissue reduction element in fluid communication with the second chamber, the tissue reduction element including a blade assembly moveable to produce a reduced adipose tissue and push the reduced adipose tissue distally;
   an mixing element in fluid communication with a distal outlet port of the first chamber and a distal outlet port of the second chamber, the mixing element including a freely rotatable member to mix the cellular matter and the reduced adipose tissue into a cellular mixture; and
   an injection element on fluid communication with the mixing element.

2. The system of claim 1, further comprising a filter element adapted to receive the reduced adipose tissue for filtering adipose tissue of a predetermined size.

3. The system of claim 2, wherein the filter element excludes reduced adipose tissue particles greater than about 1 mm in size.

4. The system of claim 1, wherein the injection element is a needle.

5. The system of claim 4, wherein the needle is of a predetermined length to promote insertion into the midcorpora of a male penis.

6. The system of claim 5, further comprising an adjustable stop element operably coupled to the needle for adjusting an insertion length of the needle.

7. The system of claim 1, wherein the blade assembly comprises a plurality of rotating blades.

8. The system of claim 1, wherein the blade assembly is drivable along a plurality of the second chamber.

9. The system of claim 1, wherein the blade assembly is operably coupled to a distal end of a rotatable drive shaft.

10. The system of claim 9, wherein a proximal end of the drive shaft is operably coupled to a drive motor for rotating the drive shaft.

11. The system of claim 9, wherein a proximal end of the drive shaft is operably coupled to a handle member for manual rotation of the drive shaft.

12. The system of claim 1, further comprising a first plunger device moveable to push the cellular matter distally through the first chamber.

13. The system of claim 12, wherein the plunger device and the blade assembly are independently operable.

14. The system of claim 12, wherein the plunger device and the blade assembly are operable to push the cellular matter and the reduced adipose tissue simultaneously.

15. The system of claim 1, wherein the freely rotatable member of the mixing element comprises a rotatable propeller member.

16. The system of claim 1, wherein the freely rotatable member of the mixing element comprises a rotatable paddle member.

17. The system of claim 1, wherein the mixing element comprises a first spray nozzle for creating a stream of the cellular matter and a second spray nozzle for creating a stream of the reduced adipose tissue.

18. A method of mixing a cellular mixture, the method comprising:

filling a first chamber with a cellular matter and a second chamber with an adipose tissue, the second chamber including a tissue reduction element in fluid communication therewith, the tissue reduction element including a blade assembly;

passing the cellular matter distally through the first chamber;

moving the blade assembly to produce a reduced adipose tissue and push the reduced adipose tissue distally through the second chamber; and operating a freely rotatable member of a mixing element in fluid communication with the first and second chambers to mix the cellular matter and the reduced adipose tissue.

19. The method of claim 18, wherein moving the blade assembly comprises driving the blade assembly along a plurality of threads within the second chamber.

20. A multi-chamber mixing and injection system, comprising:

a first chamber adapted to receive a cellular matter, the first chamber having a first longitudinal axis;

a second chamber adapted to receive an adipose tissue, the second chamber having a second longitudinal axis;

a plunger device for advancing the cellular matte through the first chamber along the first longitudinal axis;

a tissue reduction element in fluid communication with the second chamber, the tissue reduction element including a blade assembly moveable to produce a reduced adipose tissue and push the reduced adipose tissue through the second chamber along the second longitudinal axis;

a mixing element in fluid communication with the first chamber and the second chamber, the mixing element including a freely rotatable member to mix the cellular matter and the reduced adipose tissue into a cellular mixture; and an injection element in fluid communication with the mixing element.

21. The system of claim 20, wherein the first longitudinal axis is parallel with the second longitudinal axis.

* * * * *